United States Patent [19]
Harris

[11] Patent Number: 5,462,514
[45] Date of Patent: Oct. 31, 1995

[54] APPARATUS FOR AIDING ERECTIONS IN MALES

[76] Inventor: Jesse Harris, 3006 Mayfair, San Antonio, Tex. 78217

[21] Appl. No.: 237,245

[22] Filed: May 4, 1994

Related U.S. Application Data

[63] Continuation of Ser. No. 993,715, Dec. 15, 1992, abandoned.

[51] Int. Cl.$^6$ .................................................... A61F 5/41
[52] U.S. Cl. ................................................. 600/38; 601/11
[58] Field of Search ............................... 600/38, 39, 41; 601/11, 9, 14

[56] References Cited

U.S. PATENT DOCUMENTS

| | | |
|---|---|---|
| 2,874,698 | 2/1959 | Sell . |
| 3,631,853 | 1/1972 | Burdette . |
| 3,744,486 | 7/1973 | Wilson . |
| 3,820,533 | 6/1974 | Jones . |
| 4,111,192 | 9/1978 | Wu .......................................... 128/38 |
| 4,378,008 | 3/1983 | Osbon, Sr. . |
| 4,718,411 | 1/1988 | Stewart . |
| 4,741,329 | 5/1988 | Marcune . |
| 4,753,227 | 6/1988 | Yanuck, Jr. ................................. 600/41 |
| 4,856,498 | 8/1989 | Osbon . |
| 4,856,499 | 8/1989 | Kelly . |
| 5,020,522 | 6/1991 | Stewart . |
| 5,083,556 | 1/1992 | Osbon et al. . |
| 5,095,895 | 3/1992 | Walsh . |
| 5,115,800 | 5/1992 | Matejevic et al. . |

FOREIGN PATENT DOCUMENTS

| 1497441 | 1/1978 | United Kingdom ..................... 600/38 |
|---|---|---|

OTHER PUBLICATIONS

The Catalyst Vacuum System, Dacomed Corporation.
Impotence The Non–Surgical Solution, Osbon Medical Systems, ErecAid Systems by Osbon, Apr., 1992.

Primary Examiner—Paul J. Hirsch
Attorney, Agent, or Firm—Charles W. Hanor

[57] ABSTRACT

An apparatus for aiding erection in men comprising an open tubular vacuum cylinder sufficiently large to contain an erect male penis and an integrally mounted electrically powered vacuum generating unit which mounts to an end of said cylinder and supplies a limited vacuum at a relatively high leakage rate and a large, sensitive, vacuum controlling valve which may be used to accurately limit the vacuum produced by the vacuum generating unit to a point safe for a user.

17 Claims, 4 Drawing Sheets

APPARATUS FOR AIDING ERECTIONS IN MALES

This application is a continuation of application Ser. No .07/993,715, filed Dec. 14, 1992, now abandoned.

FIELD OF THE INVENTION

The present invention is in the field of medical devices and more particularly those devices used to produce an erection in men.

BACKGROUND OF THE INVENTION

Male impotence is a common medical problem. It has many roots, both physical and psychological, but its effect can be devastating for the individual and very resistant to any direct "cure." Since it is the symptom, impotence, rather than the cause which is the focus of concern for the majority of sufferers, an immediate method for overcoming said impotence is highly desirable. Several such methods are now in use. One is the use of relatively stiff flexible rods surgically implanted in the penis. Another method is the implantation of slim tubular balloons in the penis rather than rods. These balloons may be inflated with fluid from a reservoir when an erection is desired.

One common method involves the use of a vacuum pump which reduces atmospheric pressure in a tube placed over the penis. This reduced pressure induces the penis to fill with blood and become erect. A constriction device such as a rubber band is then temporarily placed at the base of the penis restricting outflow of blood from the penis and the erection is thus maintained. This system is not very different from nature's normal method of producing an erection, in which blood is restricted from flowing away from the penis and it becomes distended by inflow exceeding outflow. Of course, because of the tourniquet effect of a restriction placed on the penis, it should not be left in place for too long. In practice, 20 to 25 minute applications have proven to be safe. As this is longer than natural erections can be maintained by most men, the system is satisfactory in principal.

In practice, however, there are a number of problems involved. It takes several minutes to prepare the equipment and to apply the air sealant/lubricant to the penile area and to the relevant parts of the equipment. Inflation of the penis to the proper size and hardness may then require several more minutes. After this, a constricting band must be applied at the proper tension to maintain the erection without excessive tourniquet force which might damage tissue.

The overall effect of this "time-out" is obviously quite undesirable since it affects spontaneity. It may be considered worthwhile by those who prefer the more natural feel of an erection obtained by this method over the rod-stiffening of an otherwise flaccid penis.

Known prior art patents generally comprise a hand operated vacuum pump, a vacuum limiting valve and an erection tube which has one open end and a port at the other end for connecting to the vacuum pump. There may also be a provision for mounting and releasing a constricting band. U.S. Pat. No. 4,856,498—Osbon, is a good representative of these patents in that it clearly illustrates all the foregoing components.

The Osbon Patent includes a hand-grip powered vacuum pump which draws air through a hose from an erection tube placed over the penis. This erection tube is approximately 2" in diameter, 8½" long and is closed at the rear. When the open end is placed over the penis with lubricant/sealant applied to that end where it contacts the body at the root of the penis, a sufficient seal is formed to allow a partial vacuum to be drawn inside said erection tube. Pumping the hand-vacuum device draws air from said tube through a connecting hose down to a reduced pressure preset by a vacuum-controlling valve present between the vacuum pump and the erection tube. Once the desired level of vacuum has been reached, air is automatically admitted through the valve to maintain a desired level of pressure even though the vacuum pump is still being operated.

Continuous hand pumping and vacuum control is necessary because the seal between the open end of the tube and the man's body is not efficient and also because too low a vacuum must be avoided to prevent possible tissue damage.

After sufficient time has elapsed for blood to be drawn into the penis to the extent desired for the erection, the constricting band is applied. This may consist of one or more relatively wide rubber bands which have been lubricated and placed over the erection tube very near its open end. To apply, the bands are slid off over the end of the tube and immediately constrict around the base of the penis. Another constricting device sometimes used is an elastic band similar to a "tie-wrap" which may be further tightened after application.

U.S. Pat. Nos. 4,718,411—Stewart, 5,020,522—Stewart, and 5,095,895—Walsh, each comprise the elements listed above but differ in that the erection tubes of these patents are open at both ends. The rear opening forms a seal with the hand operated vacuum producing unit during operation. In all three of these patents the vacuum producing unit is hand operated or manual with the operating strokes collinear with the erection tube centerline. There is no provision for locking the erection tube to the vacuum unit. Therefore, they must be manually held together until sufficient vacuum is built up by the hand pump to ensure a continued seal.

An object of the present invention is to provide an erection device which is easy to use and which will decrease the time spent in achieving the desired result.

Another object of the invention is to provide a relatively large volume vacuum pump in order to reduce dependency on the body-to-erection tube seal.

Yet another object is to provide an electrically powered vacuum pump so that hand pumping is not required and two hands may be employed in proper placement of the restricting band.

Another object of the invention is to reduce the need for lubricant sealer and thus to reduce the messiness of the procedure.

A further object of the invention is to provide a sensitive, reliable and non-stepped adjustable vacuum limiting function which may be preset and locked into its final adjustment.

Yet another object of the invention is to reduce the number of pads of the apparatus.

Another object is to provide parts that are easy to clean.

Another object of the invention is to produce a device comprising two cylindrical units of approximately equal size and shape so that they may be efficiently packed and/or stored in a minimum space.

SUMMARY OF THE INVENTION

The present invention comprises an erection tube which is open at both ends, a cooperating electrically driven vane vacuum pump powered by an integral motor and rechargeable battery pack, a control switch, a vacuum limiting valve, and an elastic restricting device. The vacuum limiting valve employed with this unit is located in the same plastic block which houses the vane pump and vane pump motor. This block further forms the head closure for the erection tube and is held in sealing relationship to that tube by force resulting from vacuum. Both vacuum pump and vacuum limiting valve open directly into the erection tube through the inner surface of the head closure. One passage exhausts air from the vane pump into the atmosphere and a second passage provides an entrance for air to flow into the erection tube through the vacuum limiting valve. The maintained-contact control switch allows the user to start the unit and then to release the control and use that hand for other purposes until he desires to turn the unit off. The erection tube is constructed of clear plastic in order for the user to visually monitor the progress of the erection and to judge when to apply the restricting band. The tube is furnished with a reduced diameter on the end toward the base of the penis in order to facilitate the vacuum seal and to limit the expansion required of the restricting band. This reduced diameter end has a smoothly ground finish on both its inner and outer surfaces in order to efficiently retain lubricant used to help in sliding the restricting band off the end of the tube and to ease the removal of the tube from the erect penis.

DESCRIPTION OF THE PREFERRED EMBODIMENT

Figure 1:
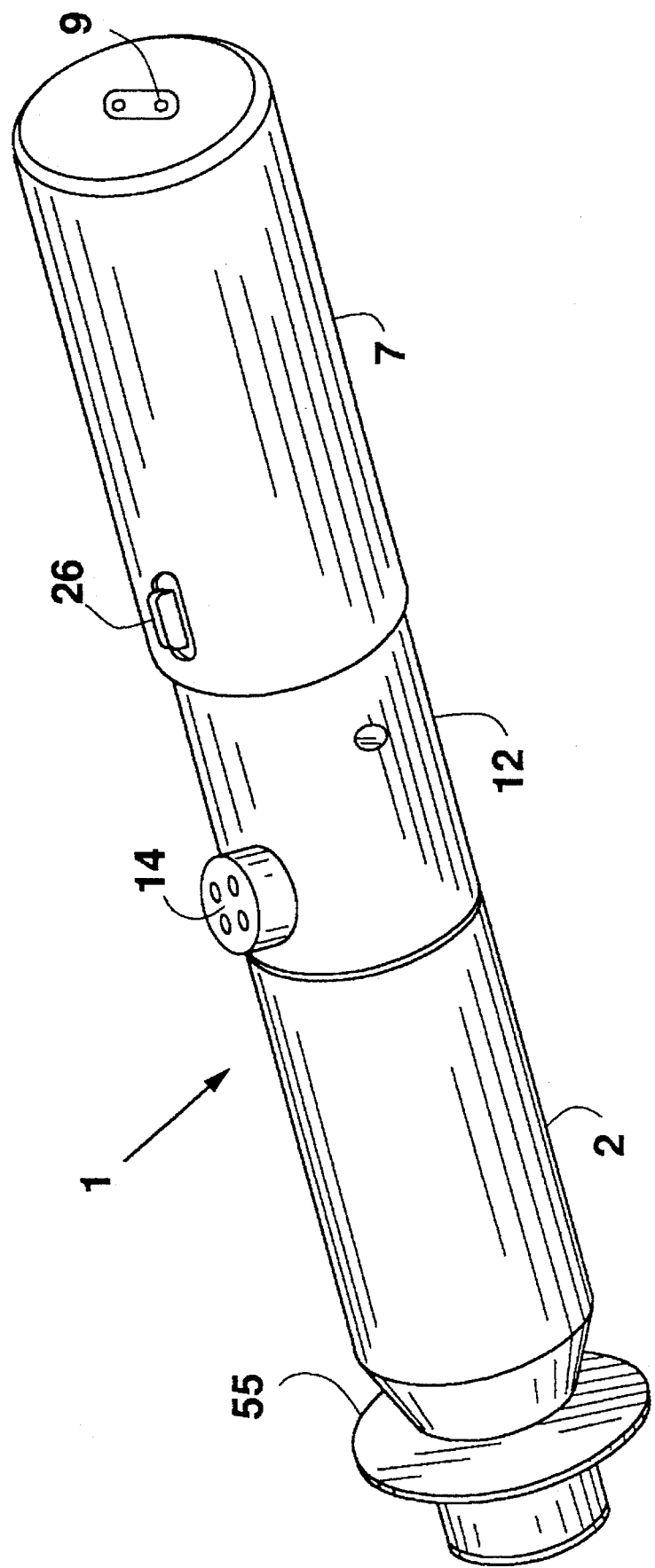
FIG. 1 is a general representation of the erection apparatus with the restriction band in place ready to be deployed.

FIG. 1 illustrates a preferred embodiment of an externally applied apparatus for aiding in the production of an erection in the human male. The assembled apparatus 1 includes a vacuum erection tube 2, a vacuum generating unit 7, and an elastic restricting band 55.

Figure 2:
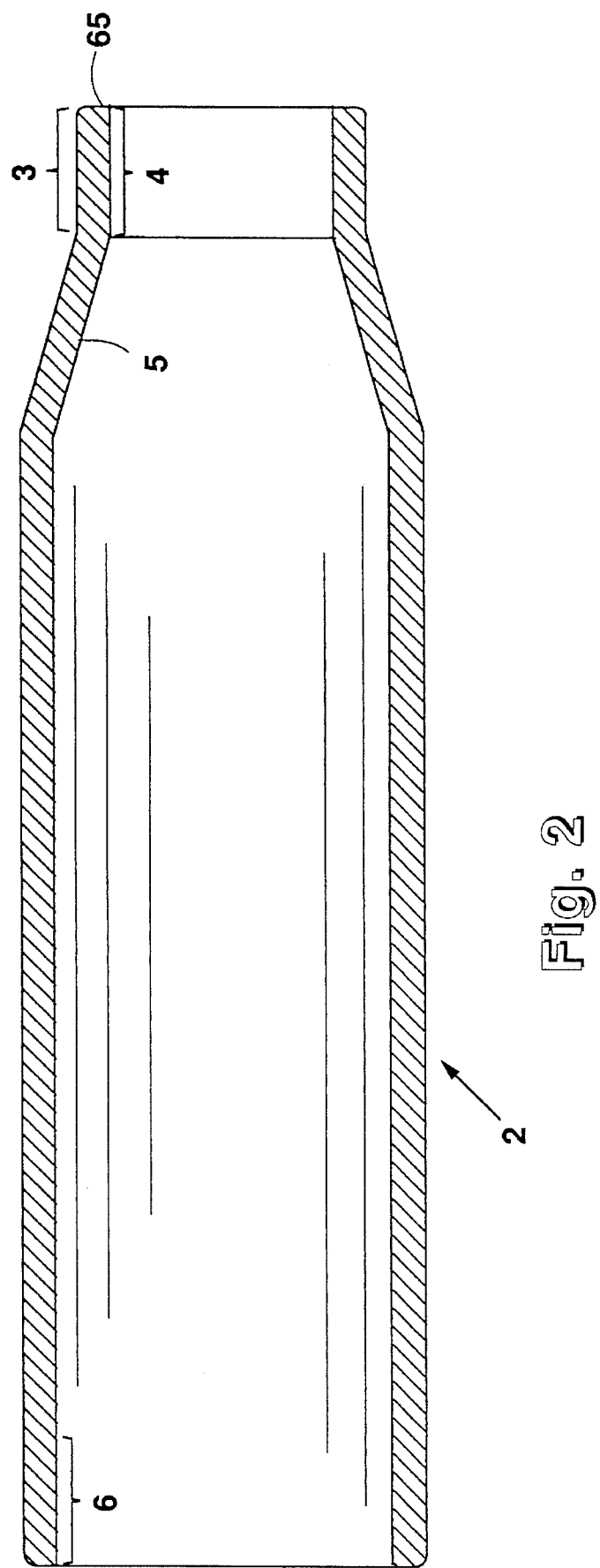
FIG. 2 is a cross sectional view of the vacuum erection tube.

FIG. 2 shows erection tube 2 in detail. It is constructed of clear plastic and is generally transparent, except for zones 3, 4 and 6 which may have a ground finish and thereby become locally semi-opaque.

Figure 3:
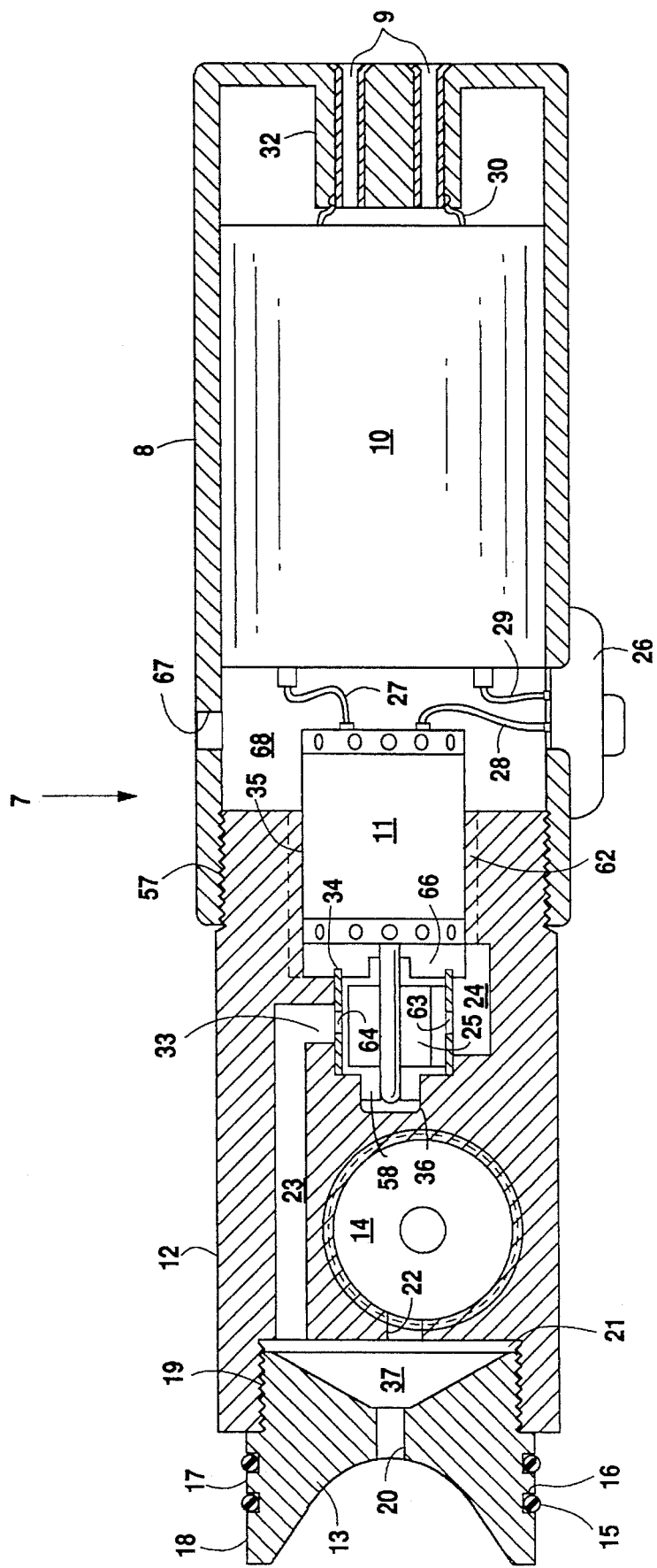
FIG. 3 is a cross sectional view of the vacuum generating unit showing relative location of all components.

The zone at 6 may be ground to form a sealing relationship with the male mating part 13 of vacuum unit 7 (see FIG. 3). Zone 3 is ground to form a smooth, lubricant retaining surface for easing the movement of an elastic restricting band thereon, and zone 4 is also ground in order to hold lubricant to facilitate the removal of the tube over an erect penis. A tapered section at 5 connects the reduced end at 3 and 4 to the full diameter body of erection tube 2. The inside surface 5 of this tapered section leads smoothly to the minimum diameter zone 4 at an included angle of approximately 30°. This angled surface, when lubricated, aids in withdrawal of the tube over the erect penis. The tapered zone is relatively short in order to maximize the area of the penis exposed to vacuum. Extreme end 65 is the area of maximum sealing against the body of the user.

FIG. 3 shows vacuum generating unit 7 having main body element 12, tubular housing 8, control switch 26, vacuum limiting valve 14, connector plug 13, motor 11, vane vacuum pump 25, storage battery 10, recharge connections 9, and interior wiring 27, 28, 29 and 30.

Tubular housing 8 connects to body element 12 by means of threaded connection 57. Connectors 9 are mounted in boss 32 of housing 8. Housing 8 also contains battery 10 and has switch 26 mounted thereon.

Main body element 12 mounts vane pump 25 in bore 34 and electric motor 11 in collinear but eccentrically located bore 35. A third bore 36, coaxial with bore 34, provides a mounting for shaft end bearing and pump end plate 58.

Vacuum pump 25 is designed to evacuate at least two cubic inches per second of air under standard conditions. Intake port 64 and discharge port 63 of vane pump 25 are located and sized so as to restrict the maximum vacuum which may be achieved. Said pods also communicate with intake bore 33 and discharge cavity 24, respectively.

Vacuum limiting valve 14 as shown in FIG. 3 communicates with volume or chamber 37 through bore or passage 22. Connector plug 13 is attached to main body element 12 by means of threaded connection 19. Outside surface 17 of plug 13 is a few thousandths of an inch smaller in diameter than the inside diameter of zone or end portion 6 of erection tube 2 so that it will fit snugly within said tube. Tapered end surface 18 facilitates the entrance of plug 13 into tube 2. One or more grooves 16 are cut in the exterior surface of plug 13 to receive o-rings 15 to form an airtight seal with erection tube 2.

Bore or passage 20 communicates volume or chamber 37 with the interior of erection tube 2 when apparatus 1 is assembled. Bores or passages 23 and 33 communicate the vane vacuum pump 25 with volume or chamber 37 and thus with the interior of erection tube 2. Volume or chamber 24 communicates vane pump 25 with the exterior of unit 1 though volume 66, multiple slots 62 around motor 11, interior volume 68 and one or more holes 67. Therefore, vane pump 25 may be rotated in the proper direction to draw air from erection tube 2 through bore 20, volume or chamber 37, bores 23 and 33, vane pump 25, and then expel that air to the atmosphere through cavity 24, volume 66, cooling slots 62, volume 68 and holes 67. Electrical safety is maximized through the use of plastic exteriors on all parts, low voltage, and integration of the motor/battery/recharge unit.

Figure 4:
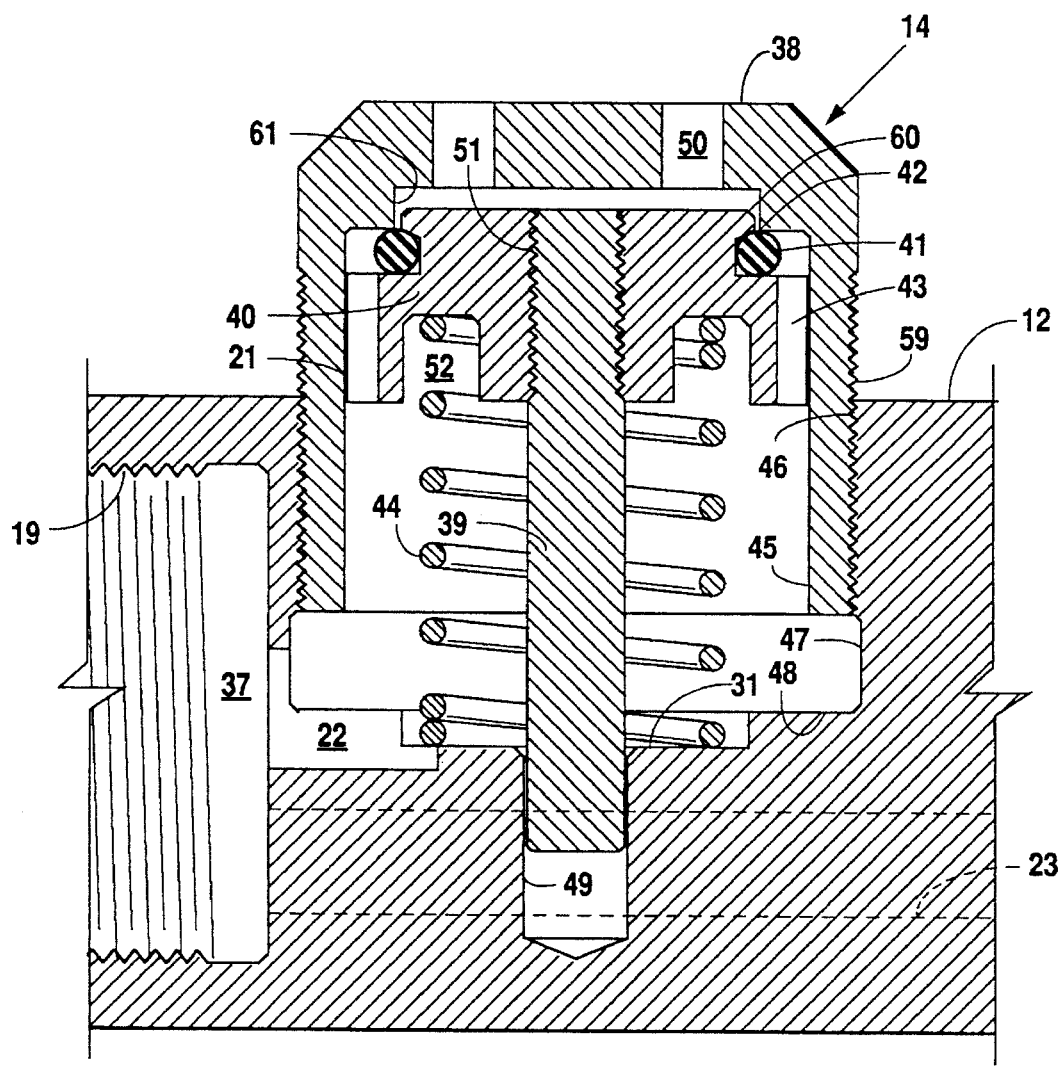
FIG. 4 is a cross sectional view of the vacuum limiting valve.

FIG. 4 shows a cross section of vacuum limiting valve 14 mounted in main body element 12. Valve housing 38 has exterior threads 59 which allow it to be screwed all the way in to contact surface 48. Threads 46 in body 12 have relief portion 47 near the bottom to avoid interference with threads 59 when cap 38 is fully screwed in. Bore hole 49 is coaxial with threads 46 and provides a guide for piston shaft 39. Piston 40 is attached to shaft 39 by threaded connection 51. Piston 40 contains an O-ring groove 42 near its upper surface which has a reduced upper diameter 60 which fits within bore 61 of housing 38. Groove 42 holds O-ring 41 which seals against the shoulder formed between bore 45 and smaller bore 61 in housing 38. Outside diameter 21 of piston 40 forms a slidable fit within bore 45 of housing 38. Piston 40 has a multiplicity of vertical grooves 43 formed in its outer surface to facilitate the passage of air thereby.

Piston 40 contains an angular groove 52 to receive and position one end of coil spring 44. The opposite end of coil spring 44 is received and positioned within bore 31 of body 12. Bore 22 communicates the lower end of the bore for threads 46 with the bore for threads 19 in main body housing 12. A multiplicity of small bores 50 in the upper end of valve housing 38 admit atmospheric air into the area above piston 40.

In operation, air pressure above piston 40 overcomes spring 44 and piston 40 moves down, breaking the seal of O-ring 41 against housing 38. Air then passes between O-ring 41 and housing 38, down through grooves 43 into the area below piston 40 and through bore 22 into volume or chamber 37. Air thus introduced below piston 40 raises the pressure below piston 40 and aids spring 44 to raise the piston and reestablish the seal. When a relatively high volume vacuum pump such as vane pump 25 is operating, the pressure below the piston 40 will raise it only enough to establish an air feed rate which holds the vacuum in volume or chamber 37 at a specific level. This level of vacuum may be raised by screwing housing 38 down, compressing spring 44 and raising its force against piston 40, or lowered by screwing it out. It is envisioned that a physician would adjust the optimum vacuum setting for each patient. Then a thread locking means such as a lock tap or thread locking compound could be used to prevent change by the user.

Figure 5:
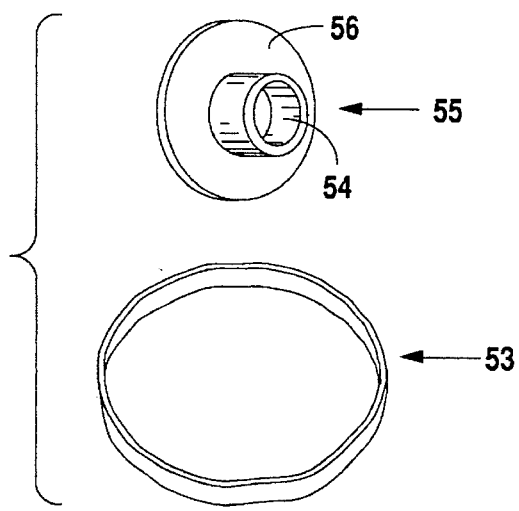
FIG. 5 shows two examples of appropriate restriction bands.

FIG. 5 illustrates two types of elastic restricting bands. Elastic blood flow restricting device 55 or a similar unit is usually applied to zone 3 by means of a lubricated application cone (not shown). Restricting device 55 is held by flange 56 and slid up an application cone mounted on tube 2 which stretches inner diameter 54 and allows it to slide onto zone 3. Band 55 is shown in place on the apparatus in FIG. 1. Bands similar to band 53 are generally stretched over the reduced end 3 of erector tube 2, crossed and reapplied across said end, forming a double wrap. This type of restricting device is generally applied manually with no mechanical aid. In both cases, lubricant on zone 3 allows the restricting device to be easily slid off over the end of tube 2 when desired.

In use, lubricant is applied to zones 3 and 4 of erector tube 2, including the extreme 65. An elastic restricting device is mounted on zone 3 and tube 2 is slipped onto mounting extension 13 of vacuum unit 7. Unit 7 is started by activating switch 26 and the assembly is slipped over the penis forming a seal between the body and tube end 65. Vacuum will then cause an erection at the rate determined by the physiology of the user and the vacuum setting determined by the physician. When the user believes that a satisfactory erection has been achieved, he pushes the restricting device off the end of tube 2, causing it to contract around the base of the penis and trap the erection until manually removed. The vacuum unit 7 is then shut off. Vacuum will dissipate in a few seconds through vacuum pump 25 and its connecting passages, so that the unit may be slipped off the erect penis. Such an erection may be safely maintained up to one half hour. Specific instruction for the individual will be made by his physician.

Clean-up of the erection tube is made easy through its open ended, obstruction free construction. The elastic restricting device is reusable after it is rinsed with warm water and toweled dry. A wipe-down of the exterior surface of the all plastic, tubular exterior of vacuum unit 7 completes the clean up.

The present invention is seen to fulfill all the objects listed for its design. A user will find a unit which is inherently safer, quicker and easier to use, to store, to transport, and to clean. This latter feature may improve the average level of hygiene for this class of device. An erection tube which is open at both ends is used both to eliminate the vacuum connecting hose and for ease of cleanup. Overheating of the pump motor is prevented by routing the air passing through the vacuum limiting valve and the seal between the man's body and the erection tube over the motor. Using an electrically powered vane type rotary vacuum pump makes possible a group of important advantages over units which require manual pumping. Volume rate of vacuum production may be increased by several hundred percent, reducing sealing requirements. Two check valves are eliminated. One hand is freed from the job of producing the vacuum and may be used to help position the device for optimum sealing and to apply the restricting band when desired. Maximum vacuum which may be produced is easily designed into a vane pump, and therefore an added safety feature is that dangerous vacuums may be avoided, should the vacuum limiting valve become blocked or inoperative. Another important advantage of the present invention is ease of clean-up. The commonly used vacuum erection tube with one open end is difficult to clean. It forms a deep narrow cup which is hard to scrub out near the bottom. Erection tubes require cleaning at each use because the sealant/lubricant must be used liberally and gets on most of the surfaces, inside and out. The small diameter hose frequently used between the pump and the erector tube also ingests lubricant particles and moisture and must be cleaned. As the present invention has fewer parts with more easily reached surfaces and requires less sealing lubricant and less handling, clean-up effort is greatly reduced. The restricting band used as part of this apparatus may be one of several types employed for such service. However, as the tube end over which it will be fitted is reduced in diameter, any given unit will suffer less stress per application and should increase its service life. Descriptions of restrictive bands and their application over erection tubes are shown in a number of patents, notably U.S. Patent 5,083,556. The art is so well known that it will not be further discussed here. Both pump/motor and erection tube units are of basically similar size and roughly tubular shape. These two units plus a small flexible restricting band and a tube of lubricant are all that is required for using this system. This reduction in number of parts and the side-by-side nesting characteristics of two cylinders minimizes the size and volume required for packing or storage. Altogether, the present invention constitutes an important advance in the utility and desirability of this class of erection device.

The foregoing is a preferred embodiment of the invention. However, various changes can be made in this system without departing from the scope of the invention. The preferred embodiment should not be interpreted as limiting the scope of the invention or claims.

I claim:

1. A vacuum and constriction apparatus for aiding male potency, comprising:

> an elongated evacuation tube of sufficient size to enclose an erect male penis for both diameter and length, open at both ends, with the fore end adapted to seal with the body of a user and the aft end adapted to connect directly to a vacuum generating unit;
>
> a vacuum generating unit having a self contained electrically driven rotary vacuum pump including a power source and a control switch;
>
> said vacuum generating unit having connector means at one end adapted to form a seal with the aft end of the elongated evacuation tube;
>
> passage means communicating the vacuum pump to the interior of the evacuation tube and to the exterior of the vacuum generating unit through which air inside said tube may be removed;

said vacuum generating unit having an adjustable, spring loaded vacuum limiting valve mounted in parallel with the vacuum pump to admit outside air into the evacuated zone when it reached the desired level of vacuum in the elongated evacuation tube; and wherein the fore end of the evacuation tube is reduced in diameter with a smooth ground finish inside and out.

2. The apparatus of claim 1, further comprising a constrictor device including an elastic band having an inner diameter adapted to restrict blood outflow through the base of the penis when atmospheric pressure is restored; and said band having sufficient elasticity to be placed over the fore end of the evacuation tube without permanent deformation.

3. The apparatus of claim 1, wherein the vacuum pump is a vane pump, sized and configured to evacuate air to a maximum vacuum of about 15 inches of mercury at a pumping rate above 2 cubic inches per second.

4. The apparatus of claim 1, wherein the evacuation tube is of clear plastic construction.

5. The apparatus of claim 1, wherein the body of the vacuum generating unit is constructed of electrically insulating material.

6. The apparatus of claim 1, wherein the control switch is of the maintained-contact type so that the vacuum pump operates until the control switch is turned off.

7. A vacuum and constriction apparatus for aiding male potency, comprising:

an elongated evacuation tube of sufficient size to enclose an erect male penis for both diameter and length, open at both ends, with the fore end adapted to seal with the body of a user and the aft end adapted to connect directly to a vacuum generating unit;

a vacuum generating unit having a self contained electrically driven rotary vacuum pump including a power source and a control switch;

said vacuum generating unit having connector means at one end adapted to form a seal with the aft end of the elongated evacuation tube;

passage means communicating the vacuum pump to the interior of the evacuation tube and to the exterior of the vacuum generating unit through which air inside said tube may be removed;

said vacuum generating unit having an adjustable, spring loaded vacuum limiting valve mounted in parallel with the vacuum pump to admit outside air into the evacuated zone when it reached the desired level of vacuum in the elongated evacuation tube;

said vacuum pump including a pump and pump motor to evacuate air from the elongated evacuation tube; and wherein the discharge air from the pump is routed to contact the pump motor to provide cooling.

8. The apparatus of claim 7, further comprising a constrictor device including an elastic band having an inner diameter adapted to restrict blood outflow through the base of the penis when atmospheric pressure is restored; and said band having sufficient elasticity to be placed over the fore end of the evacuation tube without permanent deformation.

9. The apparatus of claim 7, wherein the vacuum pump is a vane pump, sized and configured to evacuate air to a maximum vacuum of about 15 inches of mercury at a pumping rate above 2 cubic inches per second.

10. The apparatus of claim 7, wherein the evacuation tube is of clear plastic construction.

11. The apparatus of claim 7, wherein the body of the vacuum generating unit is constructed of electrically insulating material.

12. The apparatus of claim 7, wherein the control switch is of the maintained-contact type so that the vacuum pump operates until the control switch is turned off.

13. A vacuum and constriction apparatus for aiding male potency, comprising:

an elongated evacuation tube of sufficient size to enclose an erect male penis for both diameter and length, said tube being open at both ends, with the fore end adapted to seal with the body of a user and reduced in diameter with a smooth ground finish inside and out, and the aft end adapted to connect directly to a vacuum generating unit;

a vacuum generating unit having a self contained electrically driven rotary vacuum pump, said vacuum generating unit having connector means at one end adapted to form a seal with the aft end of the elongated evacuation tube;

a battery electrically coupled to the rotary vacuum pump and mounted in a tubular housing in coaxial alignment with the elongated evacuation tube;

passage means communicating the vacuum pump to the interior of the evacuation tube and to the exterior of the vacuum generating unit through which air inside said tube may be removed; and said vacuum generating unit having an adjustable, spring loaded vacuum limiting valve mounted in parallel with the vacuum pump to admit outside air into the evacuated zone when it reaches the desired level of vacuum in the elongated evacuation tube.

14. A vacuum and constriction apparatus for aiding male potency, comprising:

an elongated evacuation tube of sufficient size to enclose an erect male penis for both diameter and length, said tube being open at both ends, with the fore end adapted to seal with the body of a user and reduced in diameter with a smooth ground finish inside and out, and the aft end adapted to connect directly to a vacuum generating unit;

a vacuum generating unit having a self contained electrically driven rotary vacuum pump including a power source and a control switch;

said vacuum generating unit having connector means at one end adapted to form a seal with the aft end of the elongated evacuation tube;

passage means communicating the vacuum pump to the interior of the evacuation tube and to the exterior of the vacuum generating unit through which air inside said tube may be removed; and said vacuum generating unit having a vacuum limiting valve mounted in parallel with the vacuum pump to admit outside air into the evacuated zone when it reaches the desired level of vacuum in the elongated evacuation tube.

15. The apparatus of claim 14, wherein the power source is a rechargeable battery.

16. A vacuum and constriction apparatus for aiding male potency, comprising:

an elongated evacuation tube of sufficient size to enclose an erect male penis for both diameter and length, open at both ends, with the fore end adapted to seal with the body of a user and the aft end adapted to connect directly to a vacuum generating unit;

a vacuum generating unit having a self contained electrically driven rotary vacuum pump including a power source and a control switch;

said vacuum generating unit having connector means at one end adapted to form a seal with the aft end of the elongated evacuation tube;

passage means communicating the vacuum pump to the interior of the evacuation tube and to the exterior of the vacuum generating unit through which air inside said tube may be removed;

said vacuum generating unit having a vacuum limiting valve mounted in parallel with the vacuum pump to admit outside air into the evacuated zone when it reaches the desired level of vacuum in the elongated evacuation tube;

said vacuum pump including a pump and pump motor to evacuate air from the elongated evacuation tube; and wherein the discharge air from the pump is routed to contact the pump motor to provide cooling.

17. The apparatus of claim 16, wherein the power source is a rechargeable battery.

* * * * *